United States Patent [19]
Heya et al.

[11] Patent Number: 5,652,220
[45] Date of Patent: Jul. 29, 1997

[54] ENCAPSULATION OF TRH OR ITS ANALOG

[75] Inventors: Toshiro Heya, Hyogo; Hiroaki Okada, Osaka; Yasuaki Ogawa, Kyoto, all of Japan

[73] Assignee: Takeda Chemical Industries, Ltd., Osaka, Japan

[21] Appl. No.: 416,518

[22] Filed: Apr. 4, 1995

Related U.S. Application Data

[63] Continuation of Ser. No. 62,144, May 17, 1993, abandoned, which is a continuation of Ser. No. 882,255, May 8, 1992, abandoned, which is a continuation of Ser. No. 332,373, Apr. 3, 1989, abandoned, which is a continuation of Ser. No. 73,741, Jul. 15, 1987, abandoned.

[30] Foreign Application Priority Data

Aug. 8, 1986 [JP] Japan .................................. 61-187467

[51] Int. Cl.$^6$ ........................... A61K 38/24; A61K 38/06; A61K 47/48
[52] U.S. Cl. ............................... 514/18; 514/2; 514/963; 530/331; 424/502; 424/499; 424/490; 424/78.08
[58] Field of Search ................................ 518/18, 2, 963; 530/331; 424/502, 499, 490, 78.08

[56] References Cited

U.S. PATENT DOCUMENTS

| | | | |
|---|---|---|---|
| 4,100,152 | 7/1978 | Fujino et al. | 530/331 |
| 4,504,470 | 3/1985 | Uda et al. | 530/331 |
| 4,652,441 | 3/1987 | Okada et al. | 514/2 |
| 4,690,786 | 9/1987 | Nimomiya et al. | 514/963 |
| 4,711,782 | 12/1987 | Okada et al. | 514/963 |
| 4,917,893 | 4/1990 | Okada et al. | 514/800 |
| 4,954,298 | 9/1990 | Yamamoto et al. | 514/800 |

FOREIGN PATENT DOCUMENTS

| | | |
|---|---|---|
| 0052510 | 5/1982 | European Pat. Off. . |
| 0145240 | 6/1985 | European Pat. Off. . |
| 0190833 | 8/1986 | European Pat. Off. . |
| 1405108 | 9/1975 | United Kingdom . |

*Primary Examiner*—Ponnathapura Achutamurthy
*Assistant Examiner*—T. D. Wessendorf
*Attorney, Agent, or Firm*—Merchant, Gould, Smith, Edell, Welter & Schmidt, P.A.

[57] ABSTRACT

The present invention relates to a microcapsule containing TRH, its analog or a salt thereof and a method of producing the same which attains the release of the active ingredient stably for a prolonged period of time with high rates of incorporation of the active ingredient thereinto and with little possibility of excessive initial release or burst.

3 Claims, No Drawings

ENCAPSULATION OF TRH OR ITS ANALOG

This is a continuation of application Ser. No. 08/062,144, filed May 17, 1993 which is a continuation application of Ser. No. 07/882,255, filed May 8, 1992, which is a continuation application of Ser. No. 07/332,373, filed Apr. 3, 1989, which is a continuation application of Ser. No. 07/073,741, filed Jul. 15, 1987 now all abandoned.

This invention relates to a method of producing peptide-containing microcapsules.

Various kinds of microcapsules have already been proposed. Thus, for instance, EP Publication (laid open) No. 52,510 described microcapsules made by the phase separation method using such coacervating agents as mineral oils and vegetable oils.

However, microcapsules obtained by this method are apt to unite with one another due to particle-to-particle adhesion and/or readily assume fracture surfaces, among others, during manufacture. This may result in decreased redispersibility and increased initial burst. Furthermore, a plurality of organic solvents are used therein and residual solvents in microcapsules offer another problem.

EP Publication(laid open) No. 145,240 discloses a method of preparing microcapsules by drying in water. According to this method, drugs can be incorporated into microcapsules efficiently and drug effects resulting from sustained release properties can be expected.

In administering a drug in the form of microcapsules to a living organism, the microcapsules should meet various requirements since the drug action is highly dependent on the interaction with a function or functions intrinsic of the living organism. Therefore, it is required that microcapsules capable of meeting such varied requirements as much as possible be provided.

Under these circumstances, known microcapsules can hardly be assumed to be capable of achieving satisfactory effects as seen from the technological viewpoint.

For instance, for some drugs, the membrane structure of a microcapsule becomes relatively coarse or rough in some instances, so that a higher level of drug release than is required may take place in the initial phase, resulting in a sharp deviation from constant-rate release.

Furthermore, with drugs of certain kinds, the percentage trapping (take-up) of drugs into microcapsules becomes lower within the concentration range in ordinary use and this fact presents practical difficulties.

In view of these circumstances, the present inventors studied intensively to develop water-soluble peptide-containing, sustained release preparations and found that favorable properties of microcapsules are strongly correlated with physico-chemical properties of the drug and the drug concentration. Further studies based on this finding have now led to completion of the present invention.

Thus, the present invention provides a method of producing microcapsules which comprises causing emulsification an oil phase containing a polymer and an aqueous phase containing 2–15% by weight based on said polymer of TRH, its analog, or a salt thereof with a weak acid having a pKa of not less than 4.0 to form a w/o emulsion, mixing the emulsion with an aqueous solution of a dispersing agent to thereby form a w/o/w emulsion, and then distilling off the oil phase solvent.

The above-mentioned TRH (thyrotropin-releasing hormone) and TRH analog include, among others, pyro-2-aminoadipyl-His-thiazoline-4-carboxamide (MK-771) and compounds of the formula

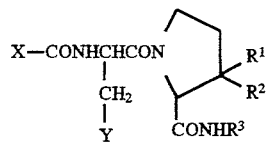

wherein X is a 4-, 5- or 6-membered heterocyclic group, Y is imidazol-4-yl or 4-hydroxyphenyl, $R^1$ and $R^2$ are the same or different and each is hydrogen or lower alkyl and $R^3$ is hydrogen or optionally substituted aralkyl.

The 4-, 5- or 6-membered heterocyclic group represented by X may have nitrogen, oxygen or/and sulfur atoms and is, for example,

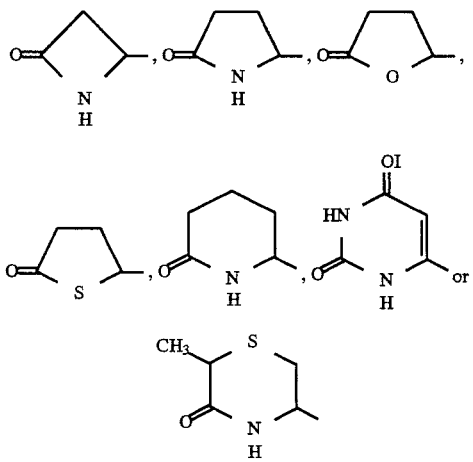

The lower alkyl represented by $R^1$ and/or $R^2$ is, for example, $C_{1-3}$ alkyl (e.g. methyl, ethyl, propyl, isopropyl).

The optionally substituted aralkyl represented by $R^3$ is, for example, hydroxy substituted phenyl-$C_{1-2}$ alkyl, e.g. 3,4-dihydroxyphenylethyl.

The compounds (I) are preferably composed of 2–4 members of the group consisting of amino acids, amino acid derivatives and amino acid analogs.

Thus, the compounds include pyroGlu-His-ProNH$_2$ (TRH), α-butyrolactonecarbonyl-His-proNH$_2$ (DN-1417), orotyl-His-proNH$_2$ (CG-3509), 2-methyl-3-oxo-tetrahydrothiazin-5-ylcarbonyl-His-Pro-NH$_2$ (CG-3703), pyroGlu-Tyr-ProNH$_2$ (Ro 10 2928), pyroGlu-His-ProNH$_2$ (3,4-dihydroxyphenylethyl) (Ro 10 9430), pyroGlu-His-(3,4-dihydroxyphenylethylaminocarbonyl) (Ro 10 8802), pyro-2-aminoadipyl-His-thiazoline-4-carboxamide (MK-771), pyroGlu-His-(3-monomethyl)ProNH$_2$(RX 74355), pyroGlu-His-(3,3-dimethyl)ProNH$_2$ (RX 77368), azetidinon-4-ylcarbonyl-His-ProNH$_2$ and so forth [for the properties of these compounds, see Neuropharmacology, 20, 947–957 (1981), ibid., 23, 339–348 (1984), Brain Research Reviews, 4, 389–403 (1982) and EP Publication(laid open) No. 123,444].

Most preferred among the compounds (I) are TRH, DN-1417 and CG-3509.

The weak acid which has a pKa (dissociation exponent) of not less than 4.0 and is capable of forming salts with the above compounds (peptides) may be either an inorganic acid or an organic acid. As the inorganic acid, there may be mentioned carbonic acid, bicarbonic acid and boric acid. The organic acid is preferably a monocarboxylic acid, preferably a lower ($C_{1-3}$) alkanemonocarboxylic acid, such as acetic acid or propionic acid.

Such weak acids preferably have a pKa of not less than 4.5 and at most a pKa of not more than 13, preferably not more than 9.5.

The polymer to be contained in the oil phase in accordance with the invention is a polymer which is sparingly soluble or insoluble in water and is biocompatible. Preferable examples are acid residue-containing polymers. Thus, there may be mentioned such biodegradable polymers as poly fatty acid esters (e.g. polylactic acid, polyglycolic acid, polylactic-glycolic acid, poly-ε-caprolactone, polycitric acid, polymalic acid), polyalkyl-α-cyanoacrylate esters (e.g. poly-butyl 2-cyanoacrylate), poly-β-hydroxylactic acid, polyalkylene oxalates (e.g. polytrimethylene oxalate, polytetramethylene oxalate), polyorthoesters (e.g. poly(3,9-dialkoxy-3,9-diethyl-2,4,8,10-tetraoxasipiro[5,5]undecan), polyorthocarbonates, other polycarbonates (e.g. polyethylene carbonate, polyethylenepropylene carbonate), and polyamino acids (e.g. poly-γ-benzyl-L-glutamic acid, poly-L-alanine, poly-γ-methyl-L-glutamic acid). As other biocompatible polymers, there may be mentioned polyacrylic acid, polymethacrylic acid, acrylic acid-methacrylic acid copolymers, dextran stearate, methylcellulose, ethylcellulose, acetylcellulose, nitrocellulose, maleic anhydride copolymers, and so forth. These polymers may be in the form of a homopolymer, a copolymer of two or more comonomers, or a simple mixture.

Preferable for use in producing injectable preparations among these polymers are biodegradable polymers, most preferable examples being polylactic acid, copolymers of lactic acid and glycolic acid, and mixtures of these. The proportions of lactic acid and glycolic acid in such copolymers are preferably such that lactic acid accounts for about 40–95 mole percent and glycolic acid for about 60–5 mole percent, more preferably such that lactic acid accounts for about 50–95 mole percent and glycolic acid for about 50–5 mole percent, and most preferably such that lactic acid accounts for about 60–90 mole percent and glycol-acid for about 40–10 mole percent.

These polymers to be used in the practice of the invention preferably have an average molecular weight of about 1,000 to about 100,000, more preferably an average molecular weight selected within the range of about 2,000 to about 50,000, especially about 5,000 to 30,000.

The solution (oil phase) containing a polymer such as mentioned above is a solution of the polymer in an organic solvent.

Said organic solvent may be any one having a boiling point of not higher than about 120° C., hardly miscible with water and capable of dissolving the polymer and thus includes, among others, halogenated alkanes (e.g. dichloromethane, chloroform, chloroethane, trichloroethane, carbon tetrachloride), ethyl acetate, ethyl ether, cyclohexane, benzene, n-hexane and toluene. These may be used also in the form of a mixture of two or more.

Dichloromethane and chloroform, which are relatively polar and have a lower boiling point, are particularly preferred.

In the first step of the microcapsule production method according to the invention, an amount corresponding to 2–15% by weight, preferably 5–12% by weight, especially 7.5–12% by weight, based on the polymer TRH or a TRH analog either in the free form or in the form of a salt with a weak acid is dissolved in water to give an internal aqueous phase. As desired, there may be added a drug-retaining substance, a pH-adjusting agent, a drug-stabilizing agent and/or a preservative provided that the interaction of the drug with the polymer will not be affected at each addition level.

As the above-mentioned drug-retaining substance, there may be mentioned substances which are soluble in water but hardly soluble in the oil phase organic solvent and either assume a highly viscous semisolid state already in the form of aqueous solutions or, when exposed to a certain external factor or factors such as the action of temperature, pH metal ions (e.g. $C^{++}$, $Al^{+++}$, $Zn^{++}$) or/and chemical condensing agents (e.g. glutaraldehyde, acetaldehyde), show marked viscosity increase to give a semisolid or solid matrix.

As examples of said drug-retaining substances, there may be mentioned naturally occurring or synthetic gums and polymers. As the pH-adjusting agent, there may be added, for instance, carbonic acid, acetic acid, oxalic acid or tartaric acid, each in the free, sodium salt or potassium salt form, hydrochloric acid or sodium hydroxide. As the stabilizing agent, there may be mentioned albumin, gelatin, citric acid, ethylenediaminetetraacetic acid sodium, dextrin, glucose, sorbitol and other sugars, glycerol and other polyols, and sodium hydrogen sulfite, among others. Examples of the preservative which may be added are parahydroxybenzoic acid esters (e.g. methylparaben, propylparaben), benzyl alcohol, chlorobutanol and thimerosal.

In the practice of the invention, it is recommended that the internal aqueous phase has a peptide weight ratio [%; (amount of peptide×100)/(amount of peptide+amount of water)] of about 5–80%, preferably 15–70%. A good result may be attained without addition of the above-mentioned drug-retaining substance under these conditions.

The thus-obtained aqueous solution, which is to serve as the internal aqueous phase, is added to a solution (oil phase) containing the polymer and then an emulsifying operation is performed to give a w/o emulsion.

Said emulsifying operation is conducted by following a dispersing method. As said method, there may be mentioned for example, the intermittent shaking method, the method which uses a mixer such as a propeller-type stirrer or a turbine-type stirrer, the colloid mill method, the homogenizer method and the sonication method.

The thus-prepared w/o emulsion is then converted to a w/o/w three-phase emulsion, which is further subjected to drying in water. Thus, said w/o emulsion is further added to an aqueous phase which is to serve as the third phase and, after formation of a w/o/w emulsion, the oil phase solvent is removed, whereby microcapsules are prepared. In preparing said w/o/w emulsion, the viscosity of the internal aqueous phase and that of the w/o emulsion influence the shape of the desired microcapsules and the percent drug trapping, among others, and therefore should preferably be adjusted such that they fall within the respective adequate viscosity ranges. In particular, the viscosity of the w/o emulsion has a great influence on the drug trapping percentage and should preferably be 150–10,000 centipoises ($1.5 \times 10^2 - 1.0 \times 10^4$ cp).

In this process and in the process of drying the w/o/w emulsion in water, the interaction between the drug and the polymer is another important factor-influencing the shape of microcapsules, the drug trapping percentage and the initial drug release. By employing the above-mentioned conditions taking the above factor into consideration, it has now become possible to prepare microcapsules further improved in drug release function.

Thus, the aqueous solution of the peptide, dissolved under the above-mentioned conditions, is made up into a w/o emulsion having an appropriate volume ratio so that the drug/polymer ratio can fall within the above-mentioned range. The emulsion is adjusted to a temperature within a certain range and then poured into an external aqueous phase maintained at a certain temperature. The subsequent removal of the organic solvent gives microcapsules. In this case, the w/o volume ratio, the w/o emulsion temperature and further the external aqueous phase temperature, among others, can influence the drug-polymer interaction and therefore optimal conditions should be employed depending on the kind and amount of drug and of polymer.

The polymer concentration in the oil phase may vary according to the kind of polymer but preferably is about 5% to 80% (w/w), especially about 30% to 60%.

The volume ratio for the w/o emulsion may vary depending on the kind and amount of drug, of polymer and of solvent. It is preferable, however, that the oil phase amounts to 1 to 200 parts, more preferably 1 to 100 parts, per part of the aqueous phase.

The temperature of the w/o emulsion and of the external aqueous phase may vary from about −10° C. to the boiling point of the organic solvent used. Generally, however, it is preferable that the emulsification be carried out within a temperature range of about 0° C. to about 35° C.

An emulsifier may be added to the external aqueous phase. Examples of the emulsifier are those generally capable of giving stable o/w emulsions, such as anionic surfactants (e.g. sodium oleate, sodium stearate sodium lauryl sulfate, etc.), nonionic surfactants [polyoxyethylenesorbitan fatty acid esters (Tween 80 & Tween 60, products of Atlas Powder, U.S.A.), polyoxyethylenecastor oil derivatives (HCO-60 & HCO-50, products of Nikko Chemicals), etc.], polyvinylpyrrolidone, polyvinyl alcohol, lecithin and gelatin. These may be used either singly or in admixture of two or more. In particular, it is preferable to use one of polyvinyl alcohol, carboxymethylcellulose and gelatin or use two or three of these combined. The emulsifier concentration may suitably be selected within the range of about 0.01% to 20%, preferably within the range of about 0.05% to 10%.

For removing the oil phase solvent in drying in water, any method in general use may be used. For instance, said method comprises simply stirring the w/o/w emulsion in a propeller-type stirrer or with a magnetic stirrer, optionally with warming and/or blowing nitrogen gas into the mixture. The solvent may also be removed by gradual depressurization or by using a rotary evaporator while adjusting the vacuum. The time required in the step of solvent removal can be shortened by gradually heating the w/o/w emulsion after the solidification of the polymer has progressed to a certain extent, to thereby make the solvent removal more complete.

The thus-obtained microcapsules are collected by centrifugation or filtration, washed repeatedly with several portions of distilled water for removing the free, water-soluble drug and so on which are adhering to the microcapsule surface and, as necessary, freeze-dried or warmed under reduced pressure for more complete removal of the moisture in the microcapsules and of the solvent in the microcapsule membrane.

If necessary, the microcapsules obtained in the above manner may be fractionated by sieving, for instance, whereby the desired particle size fraction is recovered while an excessively large microcapsule fraction is removed. For use in the form of a suspension, the microcapsules may have any particle size within the range in which the dispersibility thereof and the rate of needle penetration thereinto are satisfactory, for example an average diameter within the range of about 0.5–400 µm, preferably within the range of about 2–100 µm, as selected according to the extent of sustained release.

Thus, in accordance with the method according to the invention, the percent trapping of the active ingredient peptide into microcapsules can be increased and microcapsules having a wall membrane which is firm and much less capable of causing excessive initial release can be produced.

The microcapsules produced by the method according to the invention are advantageous in many respects. Thus, for instance, spherical and well-featured microcapsules can be obtained, without any high-level aggregation of microcapsules with one another occurring during the manufacturing process; the step of solvent removal from the oil phase can be controlled with ease and the microcapsule surface structure (e.g. the number and the size of micropores serving as main release routes for the drug) which is decisive of the rate of drug release can be controlled thereby.

The microcapsules produced by the method according to the invention can be administered as they are to living organisms as implants. They can also be administered in various dosage forms or can be used as raw materials in the manufacture of such dosage forms.

The dosage forms mentioned above include injections, oral preparations, nasal preparations, and rectal, urethral and vaginal suppositories, among others.

In making up the microcapsules according to the invention into injections, for instance, the microcapsules according to the invention are made up into a practically usable sustained release injection in the form of an aqueous suspension together with a dispersing agent (e.g. Tween 80, HCO-60, carboxymethylcellulose, sodium alginate), a preservative (e.g. methylparaben, propylparaben), an isotonizing agent (e.g. sodium chloride, mannitol, sorbitol, glucose), and so on or in the form of an oleaginous suspension together with a vegetable oil such as sesame oil or corn oil.

Furthermore, more stable, injectable, sustained release preparations containing the above-mentioned microcapsules for use in the suspension form, other than the above-mentioned formulations, are obtained by the steps of adding one or more excipients (e.g. mannitol, sorbitol, lactose, glucose), redispersing, and solidifying by freeze drying or spray drying, with distilled water for injection or an appropriate dispersion medium being attached.

The dose of such sustained release preparations provided by the present invention may vary depending on the kind and content of the active ingredient peptide, the dosage form, the duration of drug release, the target animal [e.g. warm-blooded mammal (e.g. mouse, rat, horse, cattle, human)] and the purpose of administration but should at least correspond to the effective dose of said active ingredient. Thus, for example, the single dose for a mammal such as mentioned above can suitably be selected preferably within the range of about 0.1 mg to 100 mg per kilogram of body weight, more preferably within the range of about 0.2 mg to 50 mg per kilogram of body weight, in terms of the microcapsule weight. The volume of the suspension in administering the above-mentioned injections can suitably be selected within the range of about 0.1 to 5 ml, preferably about 0.2 to 3 ml.

In this manner, there are obtained pharmaceutical compositions prepared in the form of microcapsules and comprising a water-soluble drug in an effective dose greater than the ordinary single dose and a biocompatible polymer and capable of releasing the drug continuously over a prolonged period of time.

Among those effects which can be obtained in accordance with the invention, the formation of a firm microcapsule wall, the increase in trapping percentage, and the prevention of undue initial release as a result of a decrease in diffusion rate in the portion relatively proximal to the microcapsule surface layer are supposedly due to the interaction between the acidic residue of the polymer and the basic residue or residues of the above-mentioned peptide. Therefore, among various basic residue-containing peptides, those containing a basic group or groups which are higher in basicity and/or containing a greater number of basic groups can be prevented to a greater extent from excessive initial release and can give a higher trapping percentage. Thus, at least one basic residue such as a lysine, arginine or histidine residue may be chemically added to existing peptides or, furthermore, a peptide chain containing such basic residue may be chemically bonded to physiologically active organic compounds other than peptides so that microcapsules which are equally superior can be produced.

The sustained-release preparations produced in accordance with the invention have the following characteristic features, among others:

(1) Good sustained-release property is obtained in various dosage forms of peptides. In particular, when long-term administration of an injection is required to produce an expected therapeutic effect, the desired pharmacological effect can be obtained stably by giving an injection only once a week, a month or a year, hence the sustained release can continue for a longer period of time as compared with the conventional sustained-release preparations.

(2) When peptides are administered in the form of an injection using a biodegradable polymer, any such surgical operation as embedding is not required at all but they can be administered with ease by the subcutaneous or intramuscular route in quite the same manner as with ordinary injectable suspensions. No recovery or extraction is necessary.

(3) As compared with the conventional production method comprising making a three-phase emulsion of the w/o/w type and subjecting the same to drying in water, the method according to the invention can cause the active ingredient peptide to be incorporated into microcapsules more efficiently without adding a particular drug-retaining substance to the internal aqueous phase. Furthermore, fine, spherical and well-featured microcapsules can be obtained.

(4) Microcapsules with which the excessive initial release can be substantially reduced as compared with those produced by the conventional method comprising preparing a w/o/w emulsion and subjecting the same to drying in water. They can serve as safe and better sustained-release preparations showing a constant rate of release.

EXAMPLES

The following examples are further illustrative of the present invention.

Example 1

In 0.625 ml of water was dissolved 50–1,000 mg of TRH (free form). The solution was added to a solution of 5 g of a lactic acid-glycolic acid copolymer (lactic acid/glycolic acid=75/25; weight-average molecular weight=14,000; hereinafter referred to as PLGA for short) in 6.25 ml of dichloromethane. The mixture was stirred in a small-sized homogenizer (POLYTRON®, Kinematika, Switzerland) for 30–60 seconds The emulsion thus obtained was cooled to 18° C. and poured into 1,250 ml of a 0.25% aqueous solution of polyvinyl alcohol (PVA) as cooled to 18° C. in advance. The whole mixture was made up into a w/o/w emulsion using a turbine-type homogenizer-mixer. Then, the internal w/o emulsion was allowed to solidify by evaporating the dichloromethane while stirring the w/o/w emulsion, and the solid phase was collected by centrifugation. This was redispersed in distilled water and the drug and so on remaining free were washed off.

The microcapsules collected were freeze-dried for more complete removal of the solvent and water, whereby they assumed a powder form.

The microcapsules obtained by charging TRH in an amount of 1–20% based on PLGA and following the above procedure were tested for drug trapping percentage (percentage of amount actually incorporated into microcapsules to amount charged) and further assayed, in an in vitro dissolution test, for residual TRH in microcapsules after one day of standing in phoshpate buffer (pH 7.0) at 37° C. The results thus obtained are shown below in Table 1.

TABLE 1

| Lot | TRH concentration (a) | Trapping percentage | Residual percentage after 1 day (b) |
|---|---|---|---|
| 25 | 1 | 82.1% | 34.3% |
| 51 | 2.5 | 88.6 | 85.4 |
| 26 | 5 | 105.2 | 83.7 |
| 52 | 7.5 | 95.9 | 91.2 |
| 27 | 10 | 105.9 | 74.0 |
| 101 | 12 | 83.7 | 84.6 |
| 102 | 15 | 72.1 | 83.0 |
| 28 | 20 | 47.5 | 61.2 |

Notes:
(a) TRH weight (%) relative to PLGA.
(b) ⅓₀M phosphate buffer (pH 7.0), 37° C. (mean for n = 2).

When the concentration of TRH relative to PLGA, was 1%, the percentage of drug trapping into microcapsules was rather low and the release of the first day was as much as 65.7%. However, at concentrations of 2.5–15%, good microcapsules could be prepared; the trapping percentage was very high and the first day release (initial release) was relatively small. When the TPH concentration relative to PGLA was 20%, the trapping percentage conversely decreased and the initial release increased. This was presumably due to breakage of the w/o emulsion on the occasion of drying in water and increase in the number of aqueous channels in the polymer capsule wall formed, each resulting from the increase in the amount of the hydrophilic drug.

For comparison, microcapsules were prepared in the same manner as above except that 53 mg of TRH was dissolved in 0.5 ml of water, that a relatively increased amount, namely 4 g or 6 g, of PLGA was dissolved in 4.5 ml of dichloromethane and that the viscosity of the w/o emulsion was increased to about 2,000 cp as in the conventional method of drying in water. The proportion of TRH to PLGA was 1.33% or 0.88%, respectively. The microcapsules thus obtained showed a good trapping percentage of 77% or 98%, respectively. However, the initial release was 71% or 67%, respectively, hence could not be improved at all.

Example 2

The free form of TRH (100 mg) was dissolved in 0.5 ml of distilled water or 0.5 ml of an aqueous solution of an equimolar amount of tartaric acid, citric acid, acetic acid or hydrochloric acid, followed by addition of a solution of 5 g of PLGA in 5 ml of dichloromethane. Thereafter, the procedure of Example 1 was followed to give microcapsules containing TRH or a salt thereof. In preparing the three-phase emulsion, both the liquid phases were adjusted to a temperature of 15° C.

The trapping percentages and initial burst data for the five lots of microcapsules thus obtained are shown in Table 2.

TABLE 2

| Lot | TRH salt | % Trapping | Residual percentage after 1 day (a) |
|---|---|---|---|
| 53 | Free | 98.5 | 84.2 |
| 54 | Tartrate | 93.2 | 0 |
| 55 | Citrate | 91.8 | 0 |
| 56 | Acetate | 90.4 | 66.8 |
| 57 | Hydrochloride | 85.7 | 1.2 |

(a) Mean for n = 3.

First, the TRH incorporation was good in each case because the viscosity of the w/o emulsion was made high. On the other hand, the amount of TRH charged was relatively low in this example, namely 2% relative to PLGA, and accordingly it was anticipated that the performance characteristics of the product microcapsules would be much influenced by the salt species. However, the effects of the acid added were remarkable. Thus, while, for the free-form TRH, the first day release was only 15.8% the drug was released almost completely in the initial phase, namely to an extent of 98.8% to 100%, in the cases where tartaric acid, citric acid, and hydrochloric acid were added, respectively. On the contrary, when acetic acid, a weak acid, was added, the initial release was relatively small (33.2%); when TRH was used in an amount of 5% relative to PLGA, the initial release was good (22.6%) but somewhat higher as compared with the case of free TRH.

The above results suggest that drug-polymer interactions bring about the improvement in percent trapping due to formation of a stable w/o or w/o/w emulsion, the reinforcement of the microcapsule wall, and the reduced initial release due to inhibition of drug diffusion and release through microcapsules and that the addition of an acid having a smaller pKa than that for the lactic acid or glycolic acid residue could interfere with said interactions.

Example 3

The microcapsules obtained by the procedure of Example 1 were examined for in vitro drug release property and for in vivo drug release property after subcutaneous administration to rats (the residual drug amount in microcapsules at the site of administration was determined). The results thus obtained are shown in Table 3 and Table 4.

TABLE 3

| | In vitro release (percent residual drug in microcapsules), n = 3 | | | | |
|---|---|---|---|---|---|
| Drug | Lot | 1 day | 1 week | 2 weeks | 3 weeks | 4 weeks |
| TRH | 50 | 94.5 | 82.2 | 59.0 | 44.6 | 7.8 |

TABLE 4

| | In vivo release (percent residual drug in microcapsules), n = 3 | | | | |
|---|---|---|---|---|---|
| Drug | Lot | 1 day | 1 week | 2 weeks | 3 weeks | 4 weeks |
| TRH | 50 | 79.8 | 72.8 | 31.3 | 16.7 | 3.2 |

The above data show that the microcapsules obtained by using PLGA (lactic acid/glycolic acid ratio=75/25; average molecular weight=14,000) with free TRH charged in an amount of 5% relative to the polymer were microcapsules showing good release behavior also in vivo such that a low level of initial release was followed by well controlled release approximating zero-order release. Observation under a scanning electron microscope revealed that these microcapsules were spherical and well-featured in shape with an average diameter of 10–40 microns. The microcapsules were injectable smoothly and easily with a gauge 23–22 needle of injection when an appropriate dispersion medium was used.

Example 4

An internal aqueous phase was prepared by dissolving 50 mg to 1,000 mg of CG-3509 (free form) in 0.5 ml of water, whereas an oil phase was prepared by dissolving 5 g of PLGA in 6.25 ml of dichloromethane. The oil phase was added to the internal aqueous phase with stirring with a POLYTRON® homogenizer (Kinematika, Switzerland). The thus-obtained w/o emulsion was cooled to 15°–18° C. and poured into 1,250 ml of a 0.5% aqueous solution of gelatin as cooled to 18° C. in advance and the mixture was made up into a w/o/w emulsion using a turbine-type homogenizer-mixer. Thereafter, the w/o/w emulsion was stirred for evaporation of the dichloromethane from the oil phase, whereupon the oil phase solidified. The microcapsules thus formed were collected by centrifugation, washed with distilled water and freeze dried for complete solvent removal and dehydration. Thus were obtained CG-3509-containing microcapsules in the form of a powder.

For these microcapsules, the percentage of trapping of CG-3509 was determined and the residual CG-3509 in the microcapsules after one-day standing in phosphate buffer (pH 7.0) at 37° C. was assayed in an in vitro dissolution test. The results thus obtained are shown below in Table 5.

TABLE 5

| Lot | CG-3509 concentration (a) | Trapping (%) | Residual percentage after 1 day |
|---|---|---|---|
| 106 | 1 | 91.7 | 44.1% |
| 107 | 2.5 | 95.6 | 81.6 |
| 108 | 5 | 113.5 | 88.4 |
| 110 | 10 | 88.8 | 88.0 |
| 111 | 20 | 45.8 | 78.7 |

(a) CG-3509 weight (%) relative to PLGA.

Like the case of TRH in Example 1, the trapping percentage was high and good sustained-release microcapsules were obtained with suppressed first day release (initial release) when the CG-3509 concentration relative to PLGA was 2.5–10%.

Example 5

An internal aqueous phase was prepared by dissolving 600 mg of TRH(free form) in 0.36 ml of distilled water, whereas an oil phase was prepared by dissolving 5.4 g of PLGA in 6.7 ml of dichloromethane. Thereafter, the procedure of Example 1 was followed to give microcapsules containing TRH. In preparing the three-phase emulsion, both the liquid phase were adjusted to a temperature of 19° C.

What is claimed is:

1. A microcapsule, consisting essentially:

a wall formed of a polymer selected from the group consisting of copolymers of lactic acid and glycolic acid having an average molecular weight of about 5,000 to 30,000, wherein lactic acid accounts for about 60 to 90 mol percent of the copolymer and glycolic acid for about 40 to 10 mol percent of the copolymer; and an active agent selected from the group consisting of pyroGlu-His-ProNH$_2$, alpha-butyrolactonecarbonyl-His-Pro-NH$_2$ and orotyl-His-Pro-NH$_2$, or a salt thereof with a weak acid having a pKa of not less than 4.0;

the microcapsule being capable of being formed by a process which comprises the steps of forming a W/O emulsion from (a) an oil phase containing an oil phase solvent and said polymer and (b) an aqueous phase containing said active agent, the amount of the active agent in the aqueous phase being 5 to 12% by weight, based on the amount of the copolymer in the oil phase, mixing the W/O emulsion with an aqueous solution of a dispersing agent to form a W/O/W emulsion, and distilling off the oil phase solvent.

2. A pharmaceutical composition in the form of a microcapsule according to claim 1.

3. The microcapsule according to claim 1, wherein an average diameter of the microcapsule is within the range of about 0.5 to 400 μm.

* * * * *